United States Patent [19]

Lüder et al.

[11] Patent Number: 4,541,904
[45] Date of Patent: Sep. 17, 1985

[54] METHOD OF MANUFACTURING A MOISTURE SENSOR

[75] Inventors: Ernst Lüder, Stuttgart; Traugott Kallfass, Grossbottwar, both of Fed. Rep. of Germany

[73] Assignee: Endress U. Hauser GmbH U. Co., Fed. Rep. of Germany

[21] Appl. No.: 578,715

[22] Filed: Nov. 9, 1983

Related U.S. Application Data

[62] Division of Ser. No. 272,065, Jun. 9, 1981, Pat. No. 4,433,319.

[30] Foreign Application Priority Data

Jun. 27, 1980 [DE] Fed. Rep. of Germany ....... 3024297

[51] Int. Cl.$^4$ ............................................. C23C 15/00
[52] U.S. Cl. .................................. 204/38.3; 73/336.5; 204/56 R; 204/192 C; 204/192 F; 204/192 EC; 324/61 R
[58] Field of Search ................. 204/192 C, 192 F, 15, 204/38 A, 192 EC, 192 E, 37.1, 56 R; 427/250, 101-103; 324/61 R; 73/336.5; 338/35, 34

[56] References Cited

U.S. PATENT DOCUMENTS 3,736,242 5/1973 Schwartz et al. .................. 204/192
4,143,177 3/1979 Kovac et al. ......................... 427/79
4,358,748 11/1982 Gruner et al. .................. 338/308 X

OTHER PUBLICATIONS

L. I. Maissel et al., *Handbook of Thin Film Technology*, McGraw-Hill, New York, 1970, pp. 18-12 to 18-15.
R. W. Berry et al., *Thin Film Technology*, Van Nostrand Reinhold, New York, 1968, pp. 226-231.

*Primary Examiner*—G. L. Kaplan
*Assistant Examiner*—William T. Leader
*Attorney, Agent, or Firm*—Murray, Whisenhunt & Ferguson

[57] ABSTRACT

A moisture sensor is manufactured by applying a thin layer of tantalum oxide to a moisture insensitive substrate and placing at least two electrodes on the tantalum oxide layer. The tantalum oxide layer comprises the oxide of a highly resistive low density tantalum where the tantalum in the layer applied to the substrate has a density of less than 15 g/cm$^3$. The low density tantalum may be applied by cathode sputtering and the oxide may be formed by anodic oxidation.

40 Claims, 30 Drawing Figures

METHOD OF MANUFACTURING A MOISTURE SENSOR

This is a division of application Ser. No. 272,065, filed 6/9/81, now U.S. Pat. No. 4,433,319.

BACKGROUND AND SUMMARY OF THE INVENTION

The present invention relates to a moisture sensor comprising a thin layer of tantalum oxide applied to a moisture insensitive substrate and at least two electrodes placed on the tantalum oxide layer spaced apart from each other, and to a method of making such a moisture sensor.

DE-OS No. 2,728,092 describes a moisture sensor which comprises a base electrode consisting of a piece of tantalum, a tantalum oxide layer formed by anodic oxidation of the tantalum piece and an outer electrode covering a portion of the tantalum oxide layer. By the use of a moisture sensitive layer of tantalum oxide on a base electrode comprising a piece of tantalum the intention is to utilise the advantageous properties of tantalum and tantalum oxide for humidity and moisture sensors and to avoid the disadvantages of earlier known moisture sensors with metal oxide layer.

The most widely used metal oxide moisture sensors comprise an aluminium oxide layer on a base electrode of aluminium. Such moisture sensors have a very good sensitivity because the aluminium oxide is very porous and therefore absorbs moisture in an amount depending on the vapour pressure of the water in the ambient atmosphere, the capacitance and the resistivity of the aluminium oxide layer varying relatively greatly in dependence upon the moisture absorbed. However, moisture sensors on an aluminium basis have an inadequate electrical long time stability, are sensitive to mechanical and chemical impurities and are not suitable for use in corrosive or oxidising surroundings. On the other hand, tantalum and tantalum oxide are very resistant to corrosion and also have other favourable properties such as good long time stability, temperature stability and mechanical robustness so that a moisture sensor on a tantalum basis should be superior to a moisture sensor on an aluminium basis.

However, practice has shown that a moisture sensor of the type known from DE-OS No. 2,728,092 having a tantalum oxide layer formed by anodic oxidation of a piece of tantalum cannot readily replace a moisture sensor on an aluminium basis. For the tantalum oxide obtained in this manner is not very porous and thus only slightly moisture sensitive. Thus, a direct use of such a moisture sensor is possible at the most only in limited areas for special cases. On the other hand, to provide a generally usable moisture sensor the tantalum oxide must be subjected to a subsequent treatment by which it is given the necessary porosity and moisture sensitivity, for example by ion implantation as already known for aluminium oxide. This requires complicated apparatus.

The aforementioned advantageous properties of tantalum and tantalum oxide ($Ta_2O_5$) have led to these materials being extensively used in the thin film technique wherein instead of bulk tantalum thin tantalum layers are formed by dust or vapour deposition on an insulating substrate (e.g. of glass or ceramic). If tantalum oxide layers are required they can be obtained by oxidation of previously applied tantalum layers. The tantalum layers may serve to form resistors and the tantalum oxide layers to form capacitor dielectrics. A distinction is made between two modifications of the thin tantalum layers formed by dust or vapour deposition which do not differ appreciably from bulk tantalum as regards their density and resistivity, i.e. an α-modification and a β-modification. Compared with bulk tantalum the following values apply for these modifications:

|  | Density $g/cm^3$ | Resistivity $\mu \Omega \cdot cm$ |
|---|---|---|
| Bulk tantalum | 16.6 | 13 |
| Thin layer α-modification | 15.6 | 25–50 |
| Thin layer β-modification | 15.9 | 180–220 |

Due to the substantially same density of the metal the oxides of the α-modification and of the β modification also do not differ appreciably from the oxide of the bulk tantalum. In particular, these oxides are also not very porous and thus not very moisture sensitive. The low moisture sensitivity is precisely one of the reasons why the oxides of the α and β-modifications are preferably employed as capacitor dielectrics in thin layer capacitors or in integrated thin film circuits.

If however it were desired to use the oxide of the α or β-modification of thin tantalum layers in a moisture sensor, it would have to be subjected to a similar subsequent treatment to the oxide of the bulk tantalum. The process steps necessary for this purpose would be incompatible with the usual thin film technique and could also not be carried out in existing apparatus for the production of thin film components.

The objective of the present invention is to provide a moisture sensor which has all the advantages of the moisture sensors on a tantalum basis but as regards sensitivity and measuring range is comparable to the moisture sensors on an aluminium basis and can be made with relatively simple process steps compatible with the conventional thin film technique.

Proceeding from a moisture sensor of the type set forth at the beginning this objective is achieved according to the invention in that the tantalum oxide film consists of the oxide of the highly resistive tantalum of low density.

The moisture sensor according to the invention is based on the use of the oxide of a special modification of tantalum which is also only present in thin films but which differs substantially from the previously mentioned α and β-modifications and also from bulk tantalum as regards structure, density and resistivity. This modification is described in the following English-language publications where it is referred to as "low density" tantalum:

1. "Handbook of Thin Film Technology" by L. I. Maissel and R. Glang, McGraw Hill, 1970, pages 18-12 to 18-15;

2. "Thin Film Technology" by R. W. Berry and Van Nostrand Reinhold, N.Y., 1978 pages 226 to 231.

As apparent from these publications the low density tantalum is formed under certain conditions in thin layers in the sputtering of tantalum, and the sputtering voltage, i.e. the accelerating voltage of the argon ions and the partial pressure of argon, have been found to be essential parameters. With decreasing sputtering voltage the density of the tantalum in the deposited thin layer drops to values which are below 14 $g/cm^3$ and can be as low as almost 10 $g/cm^3$ whilst the resistivity rises to values which are already 5,000μΩcm and more; values of up to 40,000μΩcm can be achieved.

Because of these two properties distinguishing the "low density tantalum" from the α and β-modifications and from bulk tantalum, this material will be called here "highly resistive tantalum of low density".

The present invention is based on the recognition that the oxide of the highly resistive tantalum of low density as regards mechanical strength, chemical resistance and electrical long time stability has similar favourable properties to those of ordinary tantalum oxide but differs from the latter in a porous structure rendering it particularly moisture sensitive. Thus, a moisture sensor can be obtained directly by oxidising a thin layer of highly resistive tantalum of low density, for example by anodic oxidation. The tantalum oxide layer thus obtained is suitable, without further structural change, as moisture sensitive layer and has a moisture sensitivity comparable with that of aluminium oxide. Both the application of a thin layer of highly resistive low density tantalum and the oxidation of such a layer are method steps which are compatible with the conventional thin film technique; however, the parameters must be correspondingly modified. All the other method steps for obtaining a moisture sensor according to the invention, such as shaping and attachment of the electrodes, can be made in accordance with the conventional thin film technique in existing apparatus for this purpose.

This compatibility affords the further possibility of forming on the same substrate simultaneously with the moisture sensor also the necessary evaluating circuit in integrated thin film technique. This makes the production simpler and more economical, gives a compact structure and because of the short electrical connections also gives better properties. By using the method known from DE-PS No. 2,714,034 for setting the temperature coefficient of thin film circuits with tantalum and/or tantalum oxide layers it is then even possible to give the entire integrated arrangement consisting of the moisture sensor and the evaluating circuit a definite temperature dependence.

A preferred method of making a moisture sensor according to the present invention resides in that by cathode sputtering or vaporisation a layer of highly resistive low density tantalum is deposited on a moisture insensitive substrate and that the tantalum layer is converted by oxidation over at least a portion of its thickness into a tantalum oxide layer.

It is however to be emphasised that the oxide of the highly resistive low density tantalum need not necessarily be made indirectly via a thin tantalum layer. It is also possible to apply a layer of the same porous oxide also directly to the substrate, either by carrying out oxidation during sputtering or vapour deposition from a tantalum source or by depositing tantalum oxide directly by sputtering or vapour deposition. The only requirement is that in both cases the parameters must be set so that the tantalum oxide layer has the same structure as a tantalum oxide layer formed by oxidation of highly resistive low density tantalum.

The moisture sensor according to the invention may be formed with all electrode structures already known in moisture sensors with aluminium oxide layers or other moisture sensitive materials, i.e. in particular with an outer electrode in the form of a thin continuous moisture permeable metal film or also with comb electrodes lying in a plane.

A particularly advantageous embodiment of the moisture sensor according to the invention is however distinguished by a novel outer electrode with lattice structure. The metal film of the lattice electrode need not be moisture permeable and can therefore be substantially thicker and more stable. It has also been found that the effect decisive for the moisture measuring takes place mainly along the edges of the electrode which in a lattice electrode may have a very great length per unit area.

Another advantageous embodiment of the moisture sensor according to the invention comprises comb electrodes made in particular manner.

Other objects and advantages of the present invention will be apparent from the following specification and claims together with the drawings.

DETAILED DESCRIPTION OF THE PREFERRED EMBODIMENTS OF THE INVENTION

Figure 1:
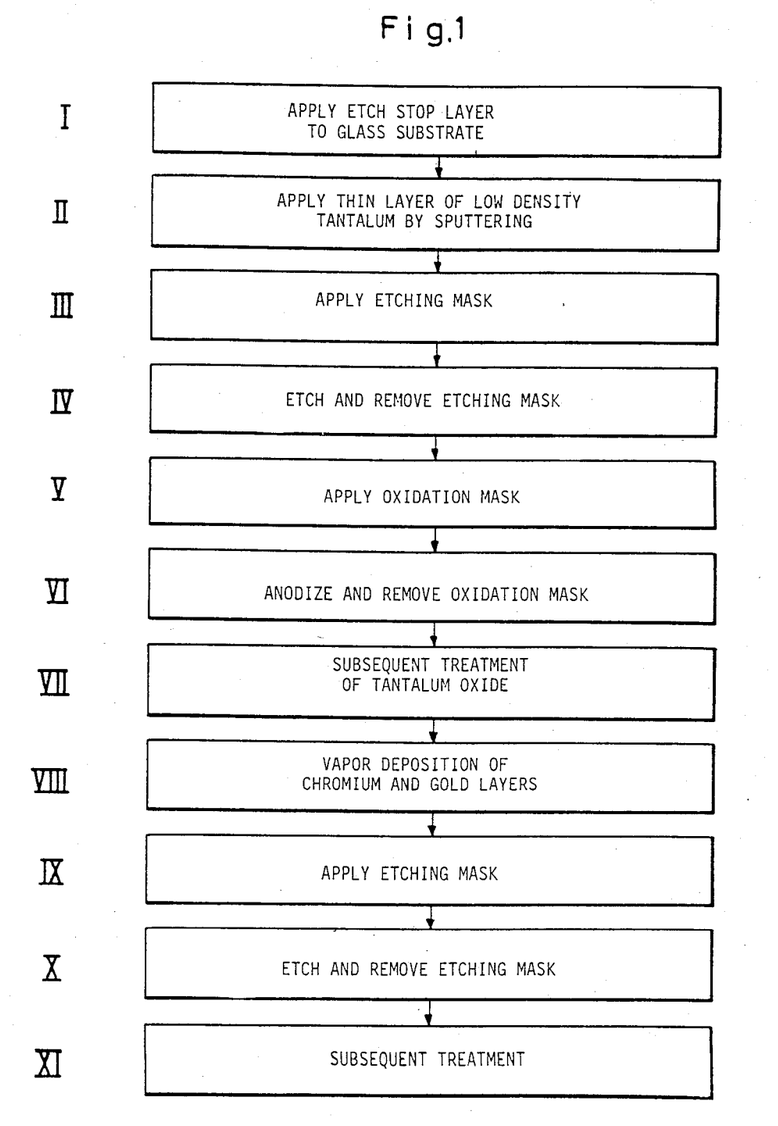
FIG. 1 is a flow diagram of the method steps of a preferred method of making a moisture sensor.

With the aid of the flow diagram of FIG. 1 and the sectional views of FIGS. 2a to 2i the production of a preferred example of embodiment of the moisture sensor illustrated in FIG. 4 in plan view will be described.

Figure 2A:
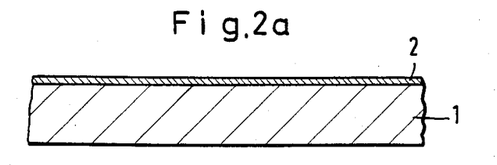
FIGS. 2a to 2i are sectional views of various production stages which arise in the production of the moisture sensor illustrated in FIG. 4 by the method of FIG. 1, the sections being made along the line A–B of FIG. 4.

Method step I proceeds from a substrate 1 comprising a moisture insensitive mechanically stable and preferably electrically insulating material, preferably glass, ceramic or a suitable plastic. If the substrate 1 consists of a material which is attacked by the chemical etchings taking place in subsequent method steps, on the top of the substrate 1 firstly an etch stop layer 2 is applied (FIG. 2a). The etch stop layer 2 is for example required when the substrate 1 consists of glass and in method step IV a wet chemical etching is carried out with hydrofluoric acid because the latter attacks glass. The etch stop layer 2 may consist of tantalum oxide $Ta_2O_5$ and be formed by applying to the glass substrate 1, which has for example a thickness of 0.6 mm, firstly a tantalum layer with a thickness of about 150 nm by sputtering in vacuum and subsequently oxidising said layer. The oxidation may be carried out in air at a temperature of about 450° C.; it should last at least 5 hours, preferably however up to 16 hours. The resulting tantalum oxide layer has a thickness of about 300 nm.

If the substrate consists of a material which is not attacked by the etching or if the shaping is conducted by a method other than etching, the etch stop layer 2 can of course be omitted; it is therefore not illustrated in the sectional views of FIGS. 2b to 2i.

Figure 2B:
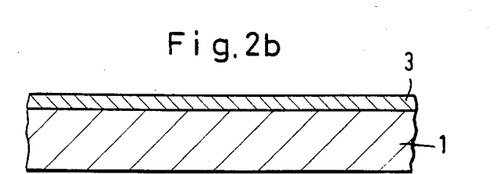

In method step II a layer 3 of highly resistive low density tantalum is applied by sputtering to the substra 1 (or, if present, to the etch stop layer 2) (FIG. 2b). A layer of highly resistive low density tantalum arises on sputtering under certain conditions, the most important parameter being the low accelerating voltage of the argon ions. This accelerating voltage is in any case substantially lower than the accelerating voltage which is normally used in sputtering bulk tantalum in the α-modification or β-modification. With a known high frequency apparatus which was operated at a frequency of about 13 MHz an accelerating voltage of about 100 V was for example used. The gas pressure was set to about 5 to 10 . $10^{-2}$ mbar and the substrate temperature to about 20° C. In larger direct current apparatuses as well with dependent DC plasma the accelerating voltage may also be of the order of magnitude of 100 to 200 V and the gas pressure may be reduced to $1.10^{-3}$ mbar and the substrate temperature increased to 200° C.

In all cases, depending on the apparatus used, the parameters in the sputtering are set so that the modification of highly resistive porous tantalum of low density known in American and English literature by the term "low density tantalum" is obtained. Whereas solid tantalum in bulk has a density of 16.6 g/cm$^3$ and a resistivity of 13$\mu\Omega$cm, the α-modification a density of 15.6 g/cm$^3$ and a resistivity of 25 to 50$\mu\Omega$cm and the β-modification a density of 15.9 g/cm$^3$ and a resistivity of 180 to 220 $\mu\Omega$cm, the density of the highly resistive porous modification, depending on the sputtering conditions, is below 15 g/cm$^3$, in particular between 11 and 13 g/cm$^3$, and the resistivity may assume very high values. So far values of the resistivity have already been achieved up to 5,000 $\mu\Omega$cm although values up to 40000 $\mu\Omega$cm are possible. With the parameters specified above for the sputtering a resistivity of about 4,000 to 5,000 $\mu\Omega$cm is achieved.

The thickness of the layer 3 of highly resistive porous tantalum is preferably between 100 and 400 nm and may for example be 200 to 300 nm.

It is possible during the deposition by sputtering of the tantalum layer 3 to conduct a doping with nitrogen or oxygen to set a desired temperature coefficient of the capacitance and/or the resistivity of the subsequently formed tantalum oxide layer.

Figure 2C:
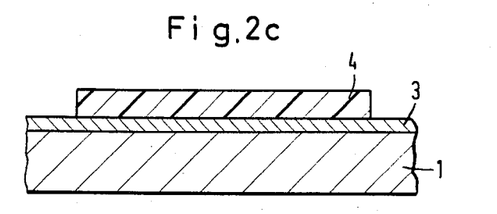

Method steps III and IV are for shaping the base electrode. For this purpose, in method step III an etching mask 4 is applied to the tantalum layer 3. This may be done in conventional manner photolithographically by covering the entire surface with a photoresist layer of 2 to 3 $\mu$m thickness, the photoresist then being exposed through a template, developed and hardened and subsequently the non-hardened portion of the photoresist removed (FIG. 2c).

Figure 2D:
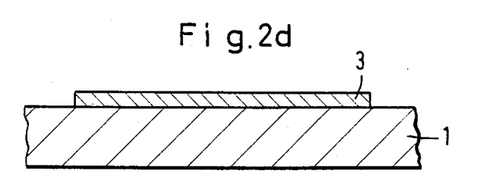
Figure 2E:
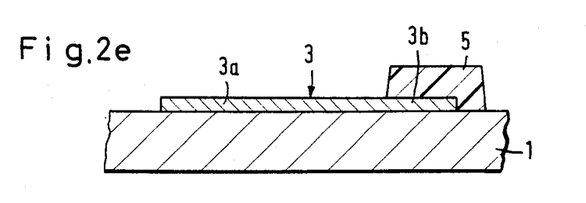

In method step IV the tantalum of the layer 3 not covered by the etching mask 4 is removed by wet chemical etching. For this purpose, a mixture of hydrofluoric and nitric acid may be used which has the following composition:
2 parts concentrated HNO$_3$
1 part 48% HF
1 part water After the etching and removal of the etching mask 4 the structure illustrated in FIG. 2 is obtained, the layer 3 of highly resistive low density tantalum having the outline illustrated in FIG. 3.

In method steps V and VI the moisture sensitive layer of tantalum oxide Ta$_2$O$_5$ is formed by anodic oxidation of a part of the highly resistive porous tantalum of the layer 3.

Figure 3:
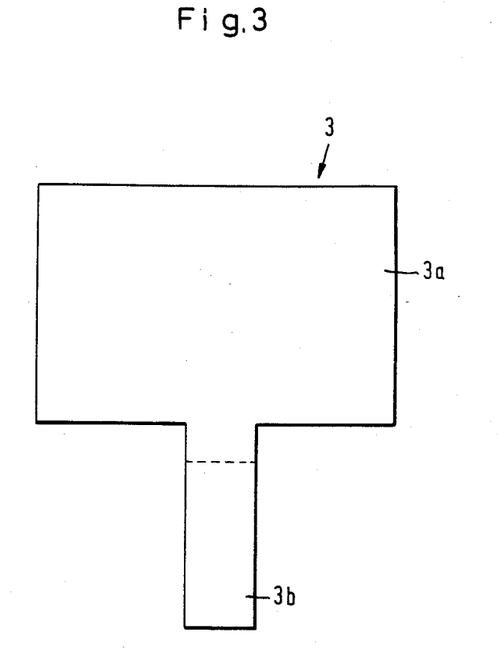
FIG. 3 is a plan view of the base electrode of the moisture sensor of FIG. 4.

For this purpose, in method step V on the tantalum layer 3 an oxidation mask 5 is applied (FIG. 2e) which leaves free the portion 3a of the layer 3 intended for the formation of the tantalum oxide layer and covers the extension 3b of the tantalum layer 3 required for the connection of the base electrode (FIG. 3). The oxidation mask can again be formed photolithographically using photoresist in the previously described manner, for example with a thickness of about 10 to 20 $\mu$m.

In method step VI the oxidation is then carried out by anodising in aqueous electrolyte. For this purpose, for example, a 0.01% citric acid may be used, the tantalum layer 3 being connected to the positive terminal of the voltage source.

Since the oxidation is not carried out on solid tantalum but on highly resistive porous tantalum the tantalum oxide obtained is also substantially less compact and more porous than ordinary tantalum oxide. This porous tantalum oxide is particularly moisture sensitive, both the dielectric constant and the resistivity varying greatly in dependence upon the moisture absorbed. On the other hand said porous tantalum oxide has however the same electrical long term stability and chemical resistance as ordinary tantalum oxide.

Whereas the usual anodisation is carried out with constant area current of about 0.1 to 1 mA/cm$^3$ it has been found that in the present case it is favourable to start the anodisation with a substantially more intense area current and to reduce the latter in the course of the anodisation to 1/20 to 1/100 of the initial value. For example, anodisation can be carried out with a constant current of 10 mA/cm$^2$ until the anodisation voltage has reached a value of 50 V; thereafter, the current is reduced to 0.1 mA/cm$^2$ and the anodisation continued with this constant current until an anodisation voltage of 150 V is reached. Thereafter, the anodisation is completed at a constant voltage of 150 V until the area current has dropped to a strength of about 5 to 1 $\mu$A/cm$^2$. This step produces a particularly loose oxide at the surface.

The oxidation is carried out only over part of the thickness of the portion 3a of the layer 3 so that beneath the tantalum oxide layer 6 obtained (FIG. 2f) a layer remains of highly resistive porous tantalum which serves as base electrode. The tantalum oxide inflates in the oxidation to about twice the thickness of the oxidise metal. In general a thickness of the tantalum oxide layer between about 100 nm and 400 nm is desired. If the tantalum layer 3 originally has a thickness of 300 nm the oxidation may be carried out over half this thickness so that a tantalum oxide layer 6 of about 300 nm thickness is achieved beneath which there is a base electrode comprising highly resistive porous tantalum having a thickness of about 150 nm. The portion 3b of the tantalum layer 3 not covered by the oxidation mask 5 is not oxidised and thus retains its original thickness.

Figures 2F, 2G:
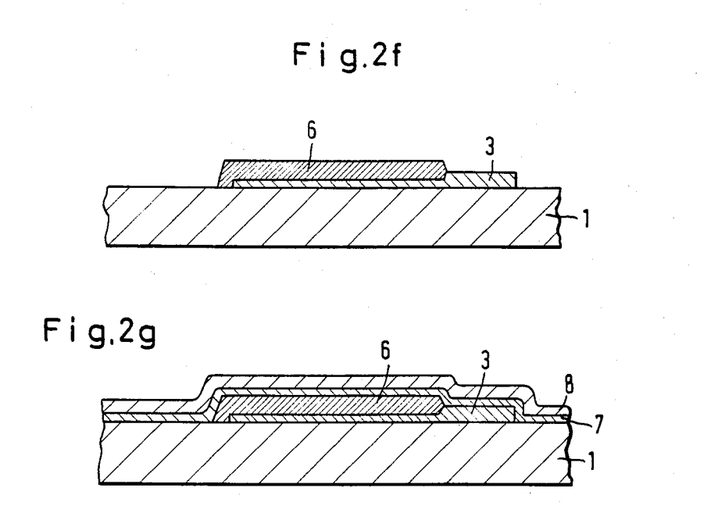

After removal of the oxidation mask 5 the structure has the appearance illustrated in FIG. 2f.

In the method step VII a subsequent treatment of the oxide is carried out, in particular for purifying and stabilising. There are various possibilities for this purpose. For example, firstly an annealing in the protective gas may be carried out. Purification of the surfaces by sputter etching has proved particularly favourable. For this purpose the surface is bombarded with argon ions with a relatively low accelerating voltage, whereby the uppermost layer is removed. A small layer removal of the order of magnitude of 20 nm suffices. Because of the different etching rates the grain boundaries are emphasised. The argon ion accelerating voltage used may be about 1000 to 1500 V; this voltage is considerably below the voltages used in ion implantation which are of the order of magnitude of 20,000 V. Thus, no ion implantation takes place. The sputter etching may be carried out with a power of about 0.05 to 0.1 W/cm$^2$ for a time of up to 2 to 4 minutes. The purification and roughening of the surface provides in particular an improved bonding of the subsequently applied cover electrode.

For the subsequent treatment the oxide layer may further be heated at a temperature of 150 to 200° C. for a time of about 30 minutes, in particular to expel moisture residues.

The method step VII may be partially combined with other method steps. For example, the sputtering etching and the expulsion heating may take place in the vapour deposition apparatus in which subsequently the metal layers for the covering electrode are vapour deposited.

The vapour deposition of the metal layers for the covering electrode takes place in method step VIII. As conductive material for the covering electrode preferably gold is vapour deposited. Since however gold adheres very poorly to the tantalum oxide firstly a chromium layer 7 (FIG. 2g) is vapour deposited onto the entire surface and then the said layer covered by vapour deposition with a gold layer 8. Instead of chromium, titanium or tantalum may be used for the bonding layer. In the case of tantalum as bonding layer a symmetrically structured moisture sensor is obtained because the tantalum oxide layer lies between two tantalum layers. This gives better electrical properties, in particular a lower polarity and a higher breakdown voltage. However, it is then advisable to insert a chromium layer between the tantalum layer and the gold layer.

In the method steps IX and X the covering electrode is etched to give it the desired form and structure. For this purpose in the method step IX an etching mask is applied which covers the portions of the metal layer 7, 8 which are not to be removed so that they are not attacked by the etchant. The application of the etching mask can again take place in known manner photolithographically by applying a photoresist film, exposing said film through a template corresponding to the desired electrode contour, developing and hardening.

In method step X the etching of the metal layer and the subsequent removal of the etching mask then takes place.

The etching may take place in two successive steps; in the first step the gold of the layer 8 is etched away and in the second step the chromium of the layer 7. For the wet chemical etching the following etchants may be used:

| | |
|---|---|
| First step (gold): | 50 g ammonium cersulfate |
| | 30 ml H$_2$SO$_4$ |
| | 900 ml H$_2$O |

-continued

| | |
|---|---|
| Second step (chromium): | 400 g potassium iodide |
| | 100 g iodine |
| | 400 ml H$_2$O |

Finally, in step XI a subsequent treatment of the finished sensor is preferably carried out for stabilisation by artificial aging. This can for example take place by annealing in air at 150° C. for a time of 2 hours. If the highly resistive low density tantalum in stage II is doped with gas, the temperature and the tempering may be increased up to 300° C.

The thickness of the chromium and gold layers 7, 8 vapour deposited in step VIII depends on the final structure of the covering electrode obtained in steps IX and X. Corresponding to a technique known in moisture sensors with aluminium oxide layer the covering electrode in the present case can also be formed as a continuous metal layer which covers the entire surfin of the tantalum oxide layer. It must then be so thin that it is moisture permeable. For this purpose the chromium layer 7 is applied with a thickness of about 5 nm and the gold layer 8 with a thickness of about 10 nm.

When using such a covering electrode in the form of a thin continuous moisture permeable metal layer subsequent treatment by tempering in method step XI is not possible because the thin chromium gold layer is not stable enough and cracks.

Figure 4:
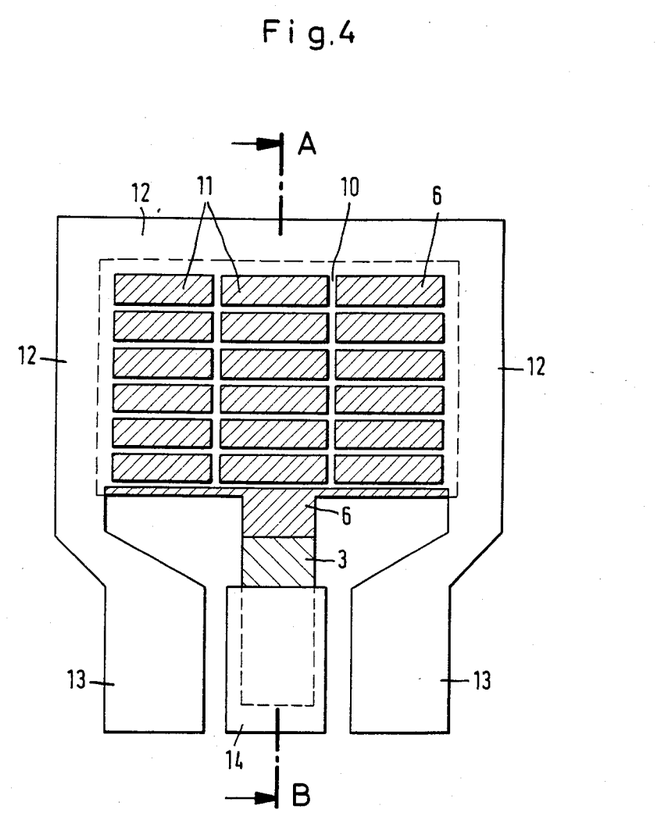
FIG. 4 is a plan view of the finished moisture sensor.

For this reason, in the example of embodiment described here a novel covering electrode with lattice structure is formed as illustrated diagrammatically in FIG. 4. This covering electrode 10 comprises intersecting longitudinal and transverse webs between which lattice windows 11 are present in which the tantalum oxide of the layer 6 is exposed so that the moisture of the surroundings has direct access. It should however be noted that for clarity in FIG. 4 the lattice windows 11 have been exaggerated in size and consequently the number of lattice windows shown is substantially less than in practice. If in the example of embodiment illustrated the active area of the moisture sensor has a length of 7 mm and a width of 4 mm, the lattice electrode 10 may have about 9000 lattice windows having a length of about 150 μm and a width of about 20 μm. The total area of the lattice windows is kept as large as possible with respect to the area covered by the metal webs of the lattice.

The contacting of the lattice electrode 10 of FIG. 4 is by integral edge regions 12 which in the example of embodiment illustrated terminate in contact areas 13 which lie on both sides of the base electrode terminal 14.

Since when using an electrode with lattice structure the moisture need not penetrate through the metal to the tantalum oxide layer, the metal layer 7, 8 in method step VIII may be applied with substantially greater thickness than in the case of a thin continuous moisture permeable covering electrode. For example, the chromium layer 7 may be given a thickness of about 0.1 μm and the gold layer 8 a thickness of about 0.2 to 0.5 μm. This thickness gives firstly a greater mechanical strength of the covering electrode, which in particular also permits the tempering in method step XI with no risk of damage; secondly, it is possible to form the covering electrode terminals 12, 13 and the base electrode terminal 14 from the same metal layers in one working operation with the covering electrode 10.

Figure 2H:
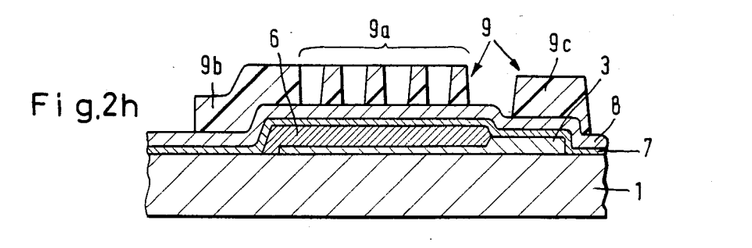

FIG. 2h shows the etching mask which is used to form the electrode structure of FIG. 4. The portion 9a provided with the passages produces the actual covering electrode 10 with the lattice webs and lattice windows. The adjoining portion 9b covers the edge regions 12 and the covering electrode terminals 13. An isolated portion 9c defines the base electrode terminal 14.

Figure 2I:
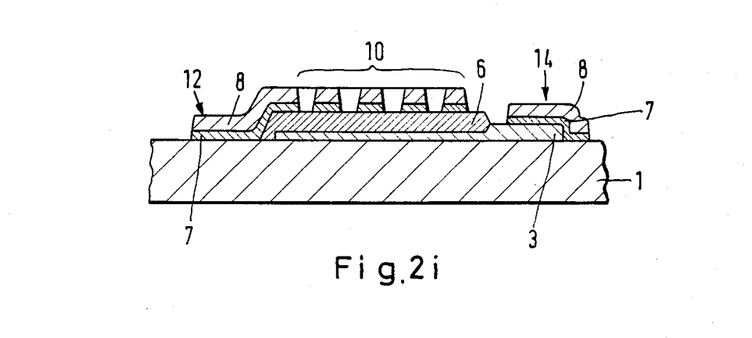

After the etching and removal of the etching mask the structure shown in FIG. 2i in section is obtained, corresponding to a section through the finished moisture sensor along the line A-B of FIG. 4.

The use of an electrode with lattice structure has been found favourable for a further reason as well. For it has been found that the phenomena important to the moisture measurement do not occur uniformly over the entire area of the moisture sensitive tantalum oxide layer 6 but occur more pronounced along the edges of the covering electrode. The lattice structure gives a very great edge length with respect to the area. For example, in the numerical example given above the covering electrode 10 having about 9000 windows with a length of 150 $\mu m$ and a width of 20 $\mu m$ gives a total edge length of 3 m for an area of 4 . 7=28 mm$^2$. This corresponds to an edge length of not more than 10 m/cm$^2$. By making the lattice structure even finer this edge length can be still further substantially increased.

Of course, the electrode with lattice structure need not have the form illustrated in FIG. 4; it may for example also be a perforated mask with round holes.

The production method described above may of course be modified in various respects without affecting the underlying idea of using as material of the moisture sensitive layer the oxide of highly electrically resistive low density tantalum.

Thus, for example, in method step II the layer 3 of highly electrically resistive low density tantalum can be deposited not by sputtering but by vapour deposition under suitable conditions. Obviously, the remaining method steps are not affected by this.

It is also possible to apply the moisture sensitive tantalum oxide layer directly to the substrate instead of forming said layer by subsequent oxidation of a layer of highly resistive low density tantalum firstly formed on the substrate. For example, the tantalum oxide layer may be obtained directly on the substrate by oxidation during the sputtering or vapour deposition of metallic tantalum in an oxygen-containing atmosphere. It is even possible to obtain a tantalum oxide layer having a structure corresponding to the oxide of highly electrically resistive tantalum of low density by sputtering or vapour deposition directly from a tantalum oxide source.

Of course, in the latter cases prior to the application of the tantalum oxide layer a base electrode must be formed on the substrate if a moisture sensor having the electrode structure previously described is to be obtained.

A further modification of the previously described production method resides in that the shaping of the covering electrode and the electrode terminals is not by subsequent etching of the applied chromium and gold layers but by the so called lift off technique using a previously applied mask.

With this technique, onto the structure obtained (FIG. 2f) by method step VII a mask is applied which represents the negative of the mask 9 illustrated in FIG. 2h so that only the areas where chromium and gold layers are subsequently necessary remain free. Thereafter, the layers of chromium and gold are vapour deposited and at the exposed areas lie on the tantalum oxide layer 6, the tantalum layer 3 and the substrate 1 but otherwise cover the mask. Finally, the mask of photoresist and the chromium and gold thereabove are dissolved away. The solvent (acetone) penetrates at the thinly vapour deposited edges of the photoresist mask through the chromium and gold.

Figure 5:
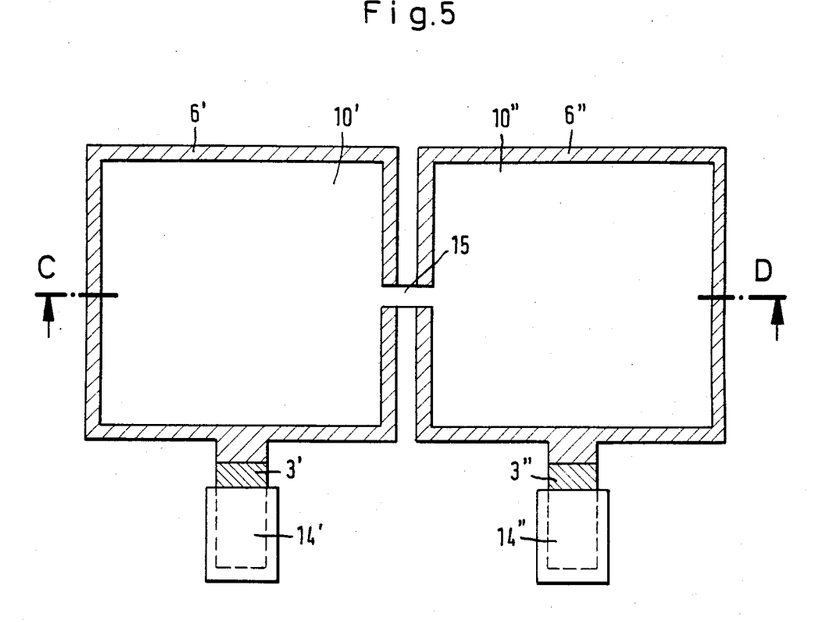
FIG. 5 is a plan view of another embodiment of the moisture sensor.
Figure 6:
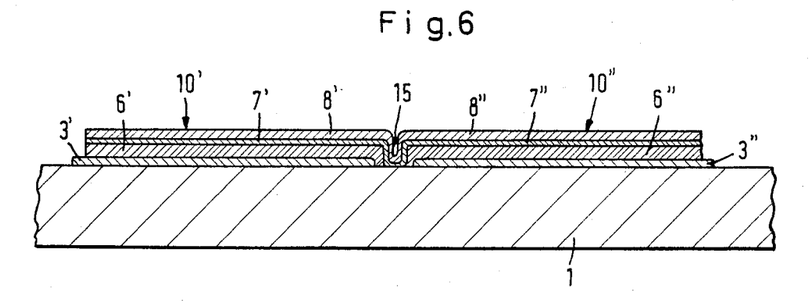
FIG. 6 is a sectional view of the moisture sensor along the line C–D of FIG. 5, FIGS. 7a to 7f are sectional views of a further embodiment of a moisture sensor in various production stages, the section being along the line E–F of FIG. 8.

A further example of embodiment of a moisture sensor which can be made with the previously described method is illustrated in plan view in FIG. 5 and in section in FIG. 6. This moisture sensor corresponds in principle to two adjacent moisture sensors of the type illustrated in FIG. 4 whose covering electrodes are connected together but have no terminals. For easier comparison the corresponding parts are provided with the same reference numerals as in FIGS. 2, 3 and 4 but for the one moisture sensor with an apostrophy and for the other moisture sensor with two apostrophies. FIG. 6 shows the common substrate 1 on which the two moisture sensors are formed a small distance apart, the layers 3' and 3" of highly resistive low density tantalum which form the base electrodes, the layer 6' and 6" which consist of the oxide of the highly resistive low density tantalum and the covering electrodes 10', 10" formed from the chromium layer 7', 7" and the gold layer 8', 8".

In the etching of the covering electrodes 10', 10" a connecting portion 15 has been left between the two covering electrodes 10' and 10". This connecting portion is kept as narrow as possible to reduce the probability of a short circuit between covering electrodes and base electrodes.

The same parts are shown in FIG. 5 which also illustrates the base electrode terminals 14', 14".

The electrodes 10', 10" may again be thin continuous moisture permeable metal layers or, as in FIG. 4, lattice electrodes.

The advantage of the embodiment of FIGS. 5 and 6 is that no connection to the covering electrodes is necessary. The connection is at the two base electrode terminals 14', 14". The two moisture sensors behave like two capacitors connected in series.

Figure 7A:
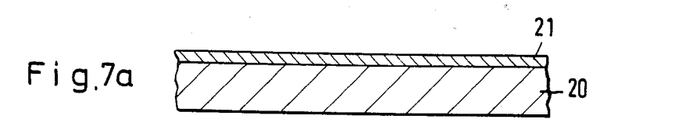
Figure 7B:
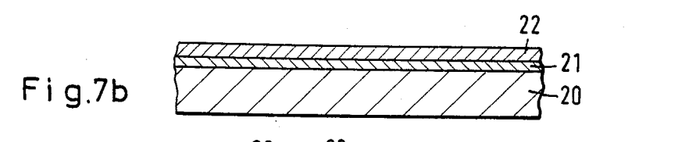
Figure 7C:
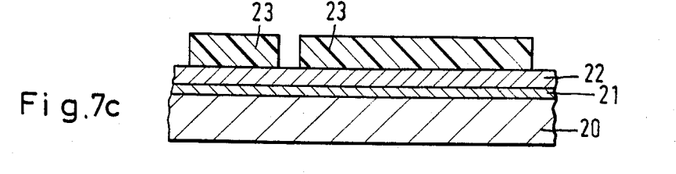
Figure 7D:
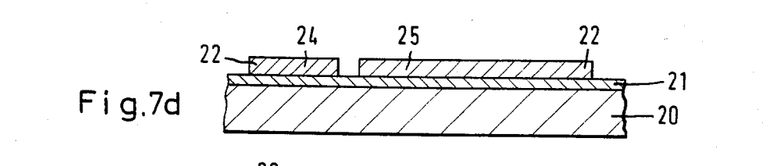
Figure 7E:
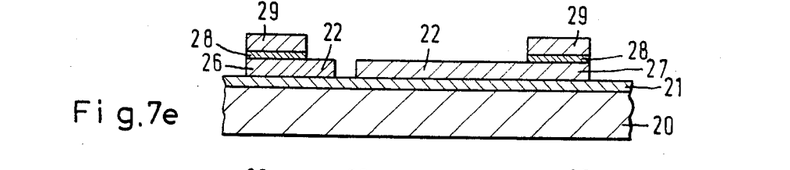
Figure 7F:
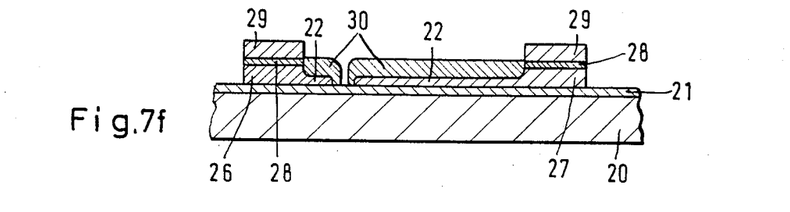
Figure 8:
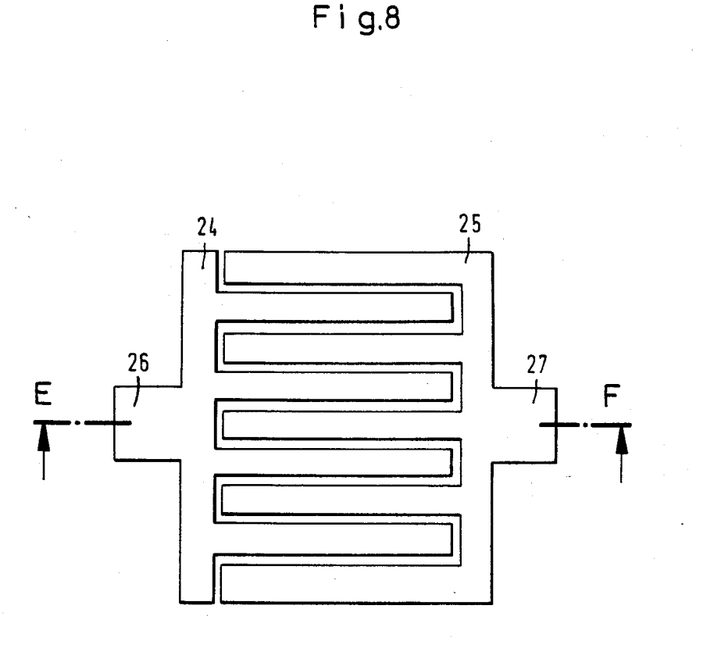
FIG. 8 is a plan view of the comb electrodes of the moisture sensor of FIG. 7, FIGS. 9a and 9b are a plan view of another embodiment of a moisture sensor with comb electrodes

Whereas the moisture sensors described hitherto have the structure of "vertical" capacitors whose electrodes lie above each other with interposition of a dielectric layer, FIGS. 7 and 8 illustrate an example of embodiment of a "horizontal" moisture sensor which comprises two comb electrodes lying in a plane and having interlacing fingers. This moisture sensor is made with a different sequence and a few modifications of the method steps of FIG. 1.

Firstly, as in method step I, on the substrate 20 (FIG. 7a) a layer 21 of tantalum oxide is formed which can also play the part of an etch stop layer if this is necessary with regard to the material of the substrate 20 and the etching method employed. Preferably, in this case the layer 21 consists of the oxide of the highly resistive low density tantalum. Thus, in method step I the parameters in the sputtering deposition of the tantalum are set so that on the substrate 20 a layer of highly resistive low density tantalum forms which on subsequent oxidation is converted to the desired moisture sensitive tantalum oxide.

As the next step, a layer 22 of highly resistive low density tantalum is applied to the tantalum oxide layer 21 in accordance with method step II (FIG. 7b).

Then, in accordance with method step III on the tantalum layer 22 an etching mask 23 of photoresist is formed (FIG. 7c) which defines the structure of the desired comb electrodes 24, 25 (FIG. 8) with the electrode terminals 26, 27.

After the etching and the removal of the etching mask according to method step IV the structure illustrated in FIG. 7d is then obtained with the comb electrodes 24, 25 of highly resistive low density tantalum exposed at the surface.

In the next method step, a chromium layer 28 and a gold layer 29 (FIG. 7e) are vapour deposited onto the electrode terminals 26 and 27, whereby the terminal contacts are obtained. This can for example be done in the previously described lift off method in that prior to the vapour deposition the entire surface of the structure except for the terminals 26 and 27 on which the vapour deposition is to take place are covered with a mask of photoresist which after the vapour deposition of the metal layers is dissolved away.

The last method step which then follows is a subsequent treatment of the comb electrodes which results in a surface oxidation of the areas of the highly resistive low density tantalum not covered by the metal layers 28 and 29. This can for example be done by tempering in air at 150° C. for the duration of one hour. As a result the exposed areas of the comb electrodes 24, 25 are covered with a layer 30 of the oxide of highly resistive low density tantalum (FIG. 7f).

In the structure obtained in this manner the comb electrodes 24, 25 are surrounded all round by the oxide of the highly resistive low density tantalum.

The comb electrodes are of course shown simplified in FIG. 8. In reality the number of interengaging fingers is very much greater to obtain once again the greatest possible edge length.

Figure 9A:
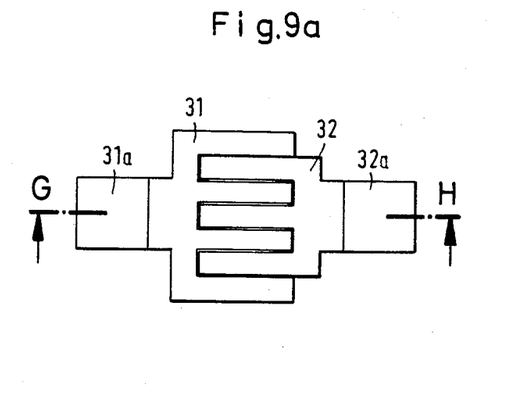
Figure 9B:
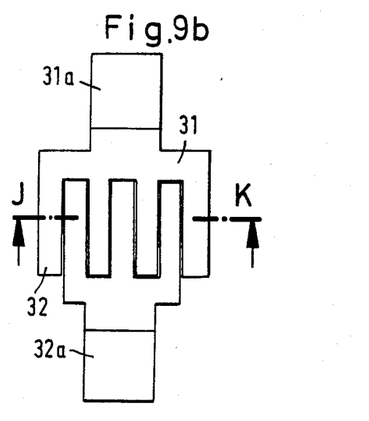

FIGS. 9a and 9b show another embodiment of a moisture sensor having two interengaging comb electrodes 31 and 32 whose production is described with reference to the sectional views of FIGS. 10a to 10g. The plan views of FIGS. 9a and 9b are identical; they are merely rotated with respect to each other through 90° to make the sectional views of FIGS. 10a to 10g easier to understand, with the sections being respectively along the line G-H of FIG. 9a and along the line J-K of FIG. 9b.

Figure 10A:
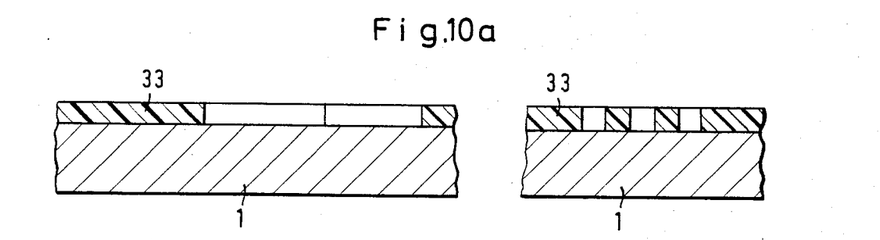
FIGS. 10a to 10g are sectional views of the moisture sensor of FIG. 9a and 9b in various production stages, taken respectively along the line G–H of FIG. 9a and along the line J–K of FIG. 9b.
Figure 10B:
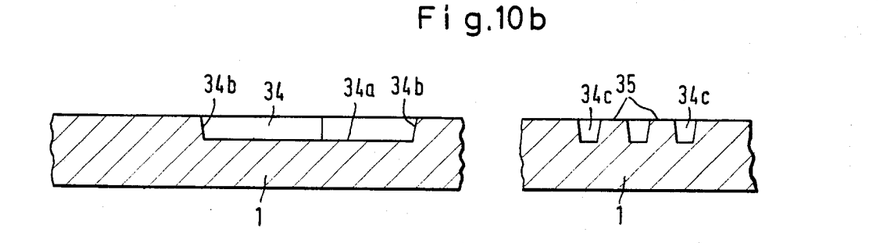

In the first method step, onto the substrate 1, consisting of boron silicate glass, an etching mask 33 is applied which leaves free only the area occupied by the one comb electrode 32. The etching mask may be formed in the manner already described from photoresist. Thereafter, the substrate 1 is etched, for example with hydrofluoric acid, so that after removal of the etching mask the structure illustrated in FIG. 10b is obtained which comprises the substrate 1 with an etched-in depression 34 which has the form of the comb electrode 32. The depth of the depression is about 1 μm. Apparent in FIG. 10 is the bottom 34a and the boundary walls 34b of the depression. The angle of inclination of the boundary walls 34b depends on the etching method employed. With wet chemical etching with hydrofluoric acid the angle of inclination is about 45°; with plasma etching substantially steeper side angles are obtained.

Also apparent in FIG. 10b are the narrow elongated portions 34c of the depression 34 corresponding to the fingers of the comb electrode and the webs 35 which are left between said portions and the upper side of which has the level of the original surface of the substrate 1.

It is pointed out here that the illustration in FIGS. 9 and 10 has been greatly simplified for clarity. In particular, the thicknesses of the various components has been very much exaggerated. The width of the portions 34c corresponding to the fingers and the width of the intermediate webs 35 is about 5 to 10 μm in each case; it is thus in reality 5 to 10 times as great as the depth of the depression 34.

Furthermore, the number of the fingers of the comb electrodes is in reality very much greater than in the illustration. In the next method step, to the upper side of the substrate 1 a layer of low density highly resistive tantalum is applied by one of the methods previously outlined, for example by sputtering with suitable setting of the parameters. The tantalum layer 36 (FIG. 10c) obtained in this manner has the previously indicated values of the density and resistivity. It is applied with a thickness which on the top of the substrate 1 and on the bottom 34a of the depression 34 is about 0.2 to 0.4 μm. However, at the steep boundary walls 34b of the depression 34 a substantially smaller thickness of the layer 36 forms. This thickness depends on the sputtering technique employed, the substrate mounting and the angle of inclination of the boundary walls 34b; it is less than half as thick as the previously indicated thickness.

Figure 10C:
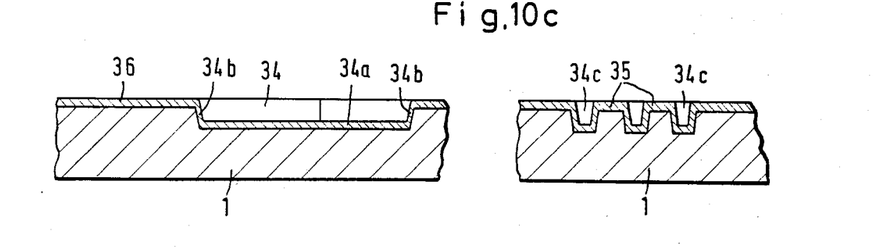
Figure 10D:
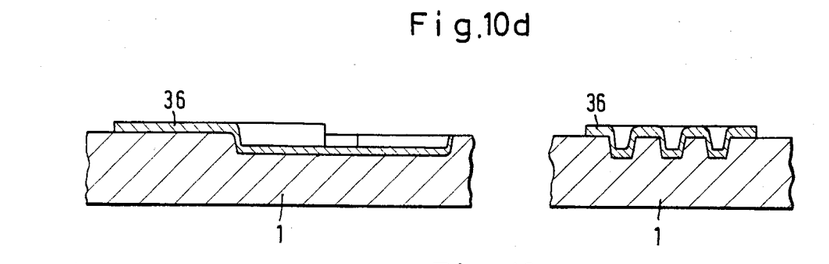

In the next method step an etching mask is applied to the structure of FIG. 10c and covers the area occupied by the two comb electrodes 31, 32 and their terminal contacts 31a, 32a (FIGS. 9a, 9b). This etching mask can once again be formed in the manner outlined by a photoresist. The tantalum not covered by the etching mask is etched away, for example in the previously described manner. After the removal of the etching mask the structure illustrated in FIG. 10d is obtained and differs from that of FIG. 10c only in that the outline of the tantalum layer 36 is restricted to the outline of the electrodes 31, 32 (FIG. 9).

Figure 10E:
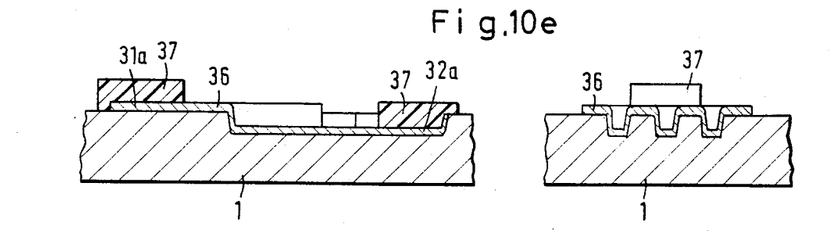

According to FIG. 10e, the next step is to apply an oxidation mask 37 to the areas of the tantalum layer 36 corresponding to the terminal contacts 31a, 32a.

Figure 10F:
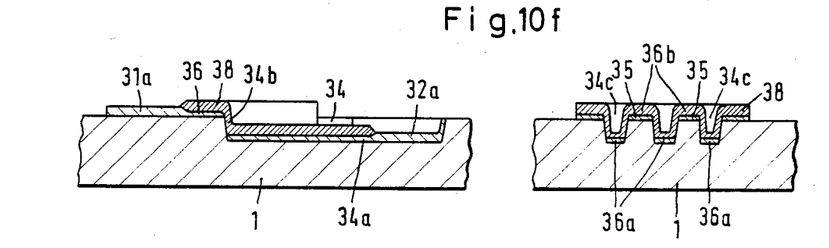
Figure 10G:
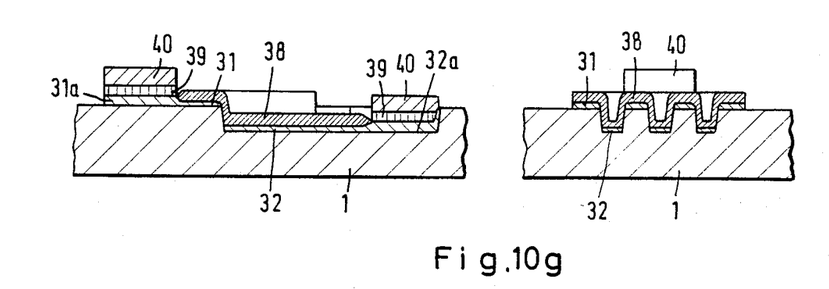

Thereafter, oxidation of the highly resistive tantalum layer 36 takes place, preferably by the previously described anodic oxidation with variation of the area current. The highly resistive low density tantalum of the layer 36 is thereby converted at the areas not covered by the oxidation mask 37 into the corresponding oxide which again inflates to about twice the thickness of the oxidised metal. This gives the tantalum oxide layer 38 which is illustrated in FIG. 10f and which consists of the oxide of highly resistive low density tantalum. The oxidation is carried out until the tantalum of the layer 36 is completely oxidised at the areas of low thickness lying on the inclined boundary walls 34b of the depression 34 but is stopped before the tantalum on the bottom 34a of the depression 34 and the top of the substrate 1 has been completely oxidised so that at these points beneath the tantalum oxide layer 38 a layer of highly resistive low density tantalum remains.

It is apparent from the right sectional view of FIG. 10f that due to this step on the bottom of the longitudinal portions 34c of the depression 34 strip-like portions 36a of tantalum remain which are completely separated from the strip-like portions 36b on the top of the webs 35, a continuous oxide layer remaining however between said strip-like portions 36a, 36b. The strip-like portions 36a lying on the bottom of the depression 34 form the fingers of the comb electrode 32 and the strip-like portions 36b lying on the top of the webs 35 form the fingers of the comb electrode 31.

The result of the oxidation is thus the forming and mutual separation of the two comb electrodes from a single tantalum layer with simultaneous formation of the tantalum oxide layer.

As already mentioned, the decisive point is that the oxidation is carried out until the tantalum layer 36 at the thin areas lying at the boundary walls 34b has been completely oxidised. The final value necessary for this purpose can be easily checked: It is achieved when the two comb electrodes 31 and 32 are isolated from each other and separate anodising currents flow in said two comb electrodes. Finally, metal layers for the terminal contacts are vapour deposited on the terminal areas 31a, 32a of the two comb electrodes 31, 32. This can again be done in the previously outlined manner by forming firstly a vapour deposition mask of photoresist which leaves free only the two terminal areas 31a, 32a and thereafter vapour depositing firstly a chromium layer 39 and then a gold layer 40. After removal of the vapour deposition mask the moisture sensor then has the finished structure illustrated in FIG. 10g.

The previously described subsequent treatment of the oxide can then be carried out for stabilising, for example by tempering in air.

In the production of this moisture sensor as well the previously described modifications can also be employed; for example, instead of the vapour deposition of the chromium layer 39 and the gold layer 40 via a mask the previously mentioned lift-off technique may be employed.

The method described with reference to FIGS. 9 and 10 permits the production of very fine comb electrodes having a large number of very fine closely adjacent fingers whose edges lie a very small distance apart, and with a large edge length.

All the moisture sensors described above are made with a small number of simple method steps which correspond to or are at least compatible with the method steps usually employed in the production of integrated thin film circuits. Thus, to make the moisture sensors existing apparatuses may be used of the type used for the production of integrated thin film circuits. Furthermore, it is readily possible to make on the same substrate which carries the moisture sensor the electronic evaluating circuit in integrated thin film technique and it is even possible to carry out some of the method steps for the production of the moisture sensor and the evaluating circuit simultaneously. For example, the resistors of the integrated thin film circuit may be formed from the highly resistive low density tantalum the printed conductors from low resistive tantalum of the α or β-modification and the capacitor dielectric from tantalum oxide of the α or β-modification.

It is further possible to form on the same substrate a heating resistor. Such a heating resistor is advantageous for preventing drop formation when using the moisture sensor in the highly humid range.

The heating resistor may be formed from tantalum of the α or β-modification or alternatively from highly resistive low density tantalum.

What we claim is:

1. A method making a moisture sensor, said method comprising applying on a moisture insensitive substrate by cathode sputtering of tantalum, a layer of highly resistive low density tantalum having a density of less than 15 g/cm$^3$, converting the tantalum layer at least over a portion of its thickness by oxidation to a tantalum oxide layer, and placing at least two electrodes on the tantalum oxide layer spaced apart from each other.

2. A method as claimed in claim 1 wherein the parameters in the application of the tantalum are so set that the tantalum in the layer applied has a resistivity of more than 4000 $\mu\Omega$ cm.

3. A method as claimed in claim 2 wherein the parameters in the application of the tantalum are so set that the tantalum in the applied layer has a resistivity of more than 10000 $\mu\Omega$ cm.

4. A method as claimed in claim 1 wherein the parameters in the application of the tantalum are so set that the tantalum in the layer applied has a density of less than 14 g/cm$^3$.

5. A method as claimed in claim 4, wherein the parameters in the application of the tantalum are so set that the tantalum in the layer applied has a density between 11 and 13 g/cm$^3$.

6. A method as claimed in claim 1 wherein a tantalum layer having a thickness between about 100 and 400 nm is applied.

7. A method as claimed in claim 1 wherein the tantalum in the application to the substrate is doped with nitrogen and/or oxygen.

8. A method as claimed in claim 1 wherein the tantalum oxide layer is formed with a thickness between 100 and 400 nm.

9. A method as claimed in claim 1 wherein the tantalum layer prior to the oxidation is given the form desired for the tantalum oxide layer or for an electrode by covering with an etching mask and subsequent etching.

10. A method as claimed in claim 1 wherein the tantalum layer is covered prior to the oxidation with an oxidation mask which leaves free only the region of the tantalum layer to be oxidised.

11. A method as claimed in claim 1 wherein the oxidation of the tantalum layer is by anodic oxidation.

12. A method as claimed in claim 11 wherein for the anodic oxidation 0.01% citric acid is used as electrolyte.

13. A method as claimed in claim 11 wherein the anodic oxidation is started with large current density and during the anodic oxidation the current density is gradually reduced.

14. A method as claimed in claim 13 wherein the current density during the anodic oxidation is reduced to about 1/20 to 1/100 of the initial value.

15. A method as claimed in claim 14 wherein the oxidation is started with a current density of about 10 mA/cm$^2$ and the current density is reduced during the anodic oxidation to about 0.1 mA/cm$^2$.

16. A method as claimed in claim 13 wherein the anodic oxidation is carried out with constant high current density until a first voltage value is reached, the current density is then reduced to a small value and the anodic oxidation is then continued with constant small value until a second higher voltage value is reached.

17. A method as claimed in claim 16 wherein the anodic oxidation is carried out with a current density of 10 MA/cm$^2$ until a voltage of about 50 V is reached and thereafter continued with a current density of about 0.1 mA/cm$^2$ until a voltage of about 150 V is reached.

18. A method as claimed in claim 16 wherein the anodic oxidation is continued after reaching the second voltage value with constant voltage until the current density has dropped to about 5 to 1 $\mu$A/cm$^2$.

19. A method as claimed in claim 1 wherein after the oxidation heating in a protective gas is carried out.

20. A method as claimed in claim 1 wherein prior to the application of the tantalum layer an etch stop layer is applied to the substrate.

21. A method as claimed in claim 20 wherein the etch stop layer is formed from tantalum oxide.

22. A method as claimed in claim 21 wherein to form the etch stop layer a layer of tantalum is applied to the substrate by sputtering or vapour deposition and the tantalum layer is subsequently converted by oxidation to a tantalum oxide layer.

23. A method of making a moisture sensor as claimed in claim 1 in which the two electrodes are in the form of comb electrodes wherein on the substrate a shallow depression is formed in the form of a comb electrode, onto the substrate surface and into the depression a layer of the highly resistive low density tantalum is applied which has the contour of the two comb electrodes, and the tantalum is oxidised over a depth which is less than the thickness of the layer in the areas lying on the substrate surface and the bottom of the depression and greater than the thickness of the layer at the boundary walls of the depression.

24. A method as claimed in claim 23 wherein the depression is formed with a depth of about 1 $\mu$m and the tantalum layer at the areas lying on the substrate surface and bottom of the depression is formed with a thickness of about 0.2 to 0.4 $\mu$m.

25. A method as claimed in claim 23 wherein the depression is formed in the substrate by etching.

26. A method as claimed in claim 23 wherein the oxidation of the tantalum layer is by anodic oxidation.

27. A method as claimed in claim 23 wherein the oxidation of the tantalum layer is continued until the tantalum layer lying on the bottom of the depression is electrically isolated from the tantalum layer lying on the substrate surface.

28. A method as claimed in claim 23 wherein prior to the oxidation of the tantalum layer the areas intended for the electrode terminals are covered by an oxidation mask.

29. A method of making a moisture sensor, said method comprising applying a layer of tantalum oxide on a moisture insensitive substrate by (a) cathode sputtering of tantalum and (b) oxidation during the sputtering, the parameters in the application being set so that the tantalum oxide layer has the same structure as a tantalum oxide layer produced by oxidation of highly resistive low density tantalum having a density of less than 15 g/cm$^3$, and placing at least two electrodes on the tantalum oxide layer spaced apart from each other.

30. A method as claimed in claim 29 wherein the tantalum oxide layer is doped during the application with nitrogen and/or carbon dioxide.

31. A method of making a moisture sensor, said method comprising applying on a moisture insensitive substrate by cathode sputtering of tantalum oxide a layer of tantalum oxide, the parameters in the application being set so that the tantalum oxide layer has the same structure as a tantalum oxide layer produced by oxidation of highly resistive low density tantalum having a density of less than 15 g/cm$^3$, and placing at least two electrodes on the tantalum oxide layer spaced apart from each other.

32. A method as claimed in claims 1, 29, or 31 wherein the tantalum oxide layer is subsequently treated by sputter etching with argon ions.

33. A method as claimed in claim 32 wherein the accelerating voltage of the argon ions is set to about 1000 V.

34. A method as claimed in claims 1, 29, or 31 wherein onto the tantalum oxide layer a continuous metal layer of less than 10 nm thickness is applied as electrode.

35. A method as claimed in claim 34 wherein to form the metal layer firstly a chromium layer is applied and then a gold layer.

36. A method as claimed in claims 1, 29, or 31 wherein onto the tantalum oxide layer a metal layer having a lattice structure with a thickness of more than 100 nm is applied as electrode.

37. A method as claimed in claim 36 wherein the metal layer is applied as continuous layer, the metal layer is covered with an etching mask and the lattice structure is formed by etching the metal layer.

38. A method as claimed in claim 36 wherein prior to the application of the metal layer on the tantalum oxide layer a mask is formed in a lattice structure, said mask being removed after the application of the metal layer.

39. A method as claimed in claim 36 wherein to form the metal layer firstly a chromium layer is applied and then a gold layer.

40. A method as claimed in claims 1, 29, or 31 for making a moisture sensor wherein on the tantalum oxide layer a layer of highly resistive low density tantalum is deposited and the two electrodes are formed in a comb structure from the highly resistive low density tantalum and are thereafter oxidised.

* * * * *